(12) United States Patent
Core et al.

(10) Patent No.: US 9,880,042 B2
(45) Date of Patent: Jan. 30, 2018

(54) PROPELLANT GAUGING TOOL FOR PREDICTING PROPELLANT MASS IN A PROPELLANT STORAGE VOLUME

(71) Applicant: THE BOEING COMPANY, Chicago, IL (US)

(72) Inventors: Steven E. Core, Redondo Beach, CA (US); Michael Novean, Valencia, CA (US); Linton Honda, Rancho Palos Verdes, CA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/962,277

(22) Filed: Dec. 8, 2015

(65) Prior Publication Data

US 2017/0160120 A1    Jun. 8, 2017

(51) Int. Cl.
| | | |
|---|---|---|
| *G01F 22/00* | (2006.01) | |
| *F17C 5/06* | (2006.01) | |
| *B64G 1/10* | (2006.01) | |
| *B64G 1/24* | (2006.01) | |
| *B64G 1/40* | (2006.01) | |
| *G01N 9/00* | (2006.01) | |
| *G01N 25/00* | (2006.01) | |

(52) U.S. Cl.
CPC ............... *G01F 22/00* (2013.01); *B64G 1/10* (2013.01); *B64G 1/242* (2013.01); *B64G 1/405* (2013.01); *G01N 9/00* (2013.01); *G01N 25/00* (2013.01)

(58) Field of Classification Search
CPC ......... G01F 22/00; G01F 9/003; B64G 1/402; B64G 1/401; B64G 1/002; F02D 19/0628; B60K 15/03; B60K 6/26; F17C 5/06; F17C 13/026; F02K 9/44
See application file for complete search history.

(56) References Cited

U.S. PATENT DOCUMENTS

| | | | | | |
|---|---|---|---|---|---|
| 4,923,152 | A * | 5/1990 | Barkats | ................. | B64G 1/401 137/256 |
| 5,027,597 | A * | 7/1991 | Soeffker | ................ | B64G 1/402 244/172.2 |
| 5,687,607 | A * | 11/1997 | Brandt | .................. | B64G 1/402 73/290 R |
| 6,055,485 | A * | 4/2000 | Eun | ....................... | B64G 1/402 340/618 |
| 8,393,582 | B1 * | 3/2013 | Kutter | ................... | B64G 1/002 244/172.2 |
| 9,334,069 | B1 * | 5/2016 | Honda | ...................... | F02K 9/44 |
| 2005/0087236 | A1 * | 4/2005 | Woo | ....................... | B60K 15/03 137/572 |

(Continued)

*Primary Examiner* — Yuri Kan
(74) *Attorney, Agent, or Firm* — Patterson + Sheridan, LLP

(57) ABSTRACT

Apparatus, computer-readable medium, and method for calculating a mass of propellant in a propellant storage volume. A density of the propellant is calculated based on a detected pressure and temperature of the propellant and actual thermodynamic properties of the propellant. A volume of the propellant storage volume is calculated based on a measured nominal volume and changes to the nominal volume based on pressure. The mass of the propellant is calculated by multiplying the calculated volume of the propellant storage volume by the calculated density of the propellant in the propellant storage volume.

20 Claims, 10 Drawing Sheets

(56) References Cited

U.S. PATENT DOCUMENTS

| | | | |
|---|---|---|---|
| 2008/0223453 A1* | 9/2008 | Carr | F02D 19/0628 137/386 |
| 2009/0057036 A1* | 3/2009 | Oxocelhay | G01F 9/003 177/25.14 |
| 2009/0234596 A1* | 9/2009 | Kawasaki | F17C 13/026 702/55 |
| 2012/0253578 A1* | 10/2012 | Utsumi | B60K 6/26 701/22 |
| 2012/0267002 A1* | 10/2012 | Kittilsen | F17C 5/06 141/4 |
| 2014/0032092 A1* | 1/2014 | Vu | B64G 1/402 701/123 |
| 2016/0200457 A1* | 7/2016 | Droppers | B64G 1/402 244/171.1 |

* cited by examiner

PROPELLANT GAUGING TOOL FOR PREDICTING PROPELLANT MASS IN A PROPELLANT STORAGE VOLUME

BACKGROUND

Aspects described herein relate to calculating a mass of gaseous propellant in a tank, and more specifically, to calculating a mass of gaseous propellant in a propellant storage volume, such as a propellant storage tank based on measured properties of the gaseous propellant.

SUMMARY

According to one aspect described herein, a satellite system includes a satellite body and a propellant storage volume storing a propellant. The satellite system also includes at least one thruster operable to expel the propellant. The satellite system also includes at least one pressure transducer arranged on the propellant storage volume and operable to measure a pressure of the propellant in the propellant storage volume. The satellite system also includes at least one temperature sensor arranged on the propellant storage volume and operable to measure a temperature of the propellant in the propellant storage volume. The satellite system also includes a controller that includes a computer processor and computer memory. The computer memory stores thermodynamic property data of the propellant. The computer memory also stores propellant storage volume data that includes known volumes of the propellant storage volume at different pressures of the propellant. The computer memory also stores a propellant mass calculation application that, when executed on the computer processor, performs an operation for processing data, comprising defining a volume of the propellant storage volume, based on at least one measured pressure from the pressure transducer and the propellant storage volume data. The operation also comprises defining a density of the propellant in the propellant storage volume, based on the at least one measured pressure from the pressure transducer, at least one measured temperature from the temperature sensor, and the thermodynamic property data. The operation also comprises calculating a mass of the propellant in the propellant storage volume, based on the defined volume and the defined density.

According to one aspect, a method for calculating a mass of propellant in a propellant storage volume includes receiving at least one measured temperature of the propellant from a temperature sensor. The method also includes receiving at least one measured pressure of the propellant from a pressure transducer. The method also includes defining a volume of the propellant storage volume by accessing a propellant volume data structure that provides known propellant storage volumes at different tank pressures and extracting from the tank volume data structure a volume corresponding to the received at least one measured pressure of the propellant. The method also includes defining a density of the propellant in the propellant storage volume by accessing a thermodynamic property data structure that provides densities of the propellant at different pressures and temperatures and extracting from the thermodynamic property data structure a density of the propellant corresponding to the received at least one measured pressure and the at least one measured temperature. The method also includes calculating a mass of the propellant in the propellant storage volume by calculating a product of the defined volume and the defined density.

According to one aspect, a computer program product for calculating a mass of propellant in a propellant storage volume includes a computer-readable storage medium having computer-readable program code embodied therewith. The computer-readable program code is executable by one or more computer processors to receive at least one measured temperature of the propellant from a temperature sensor. The computer-readable program code is also executable to receive at least one measure pressure of the propellant from a pressure transducer. The computer-readable program code is also executable to define a volume of the propellant storage volume by accessing a propellant storage volume data structure that provides known propellant storage volumes at different propellant storage volume pressures and extracting from the propellant storage volume data structure a volume corresponding to the received at least one measured pressure of the propellant. The computer-readable program code is also executable to define a density of the propellant in the propellant storage volume by accessing a thermodynamic property data structure that provides densities of the propellant at different pressures and temperatures and extracting from the thermodynamic property data structure a density of the propellant corresponding to the received at least one measured pressure and the at least one measured temperature. The computer-readable program code is also executable to calculate a mass of the propellant in the propellant storage volume by calculating a product of the defined volume and the defined density.

DETAILED DESCRIPTION

Figure 1A:
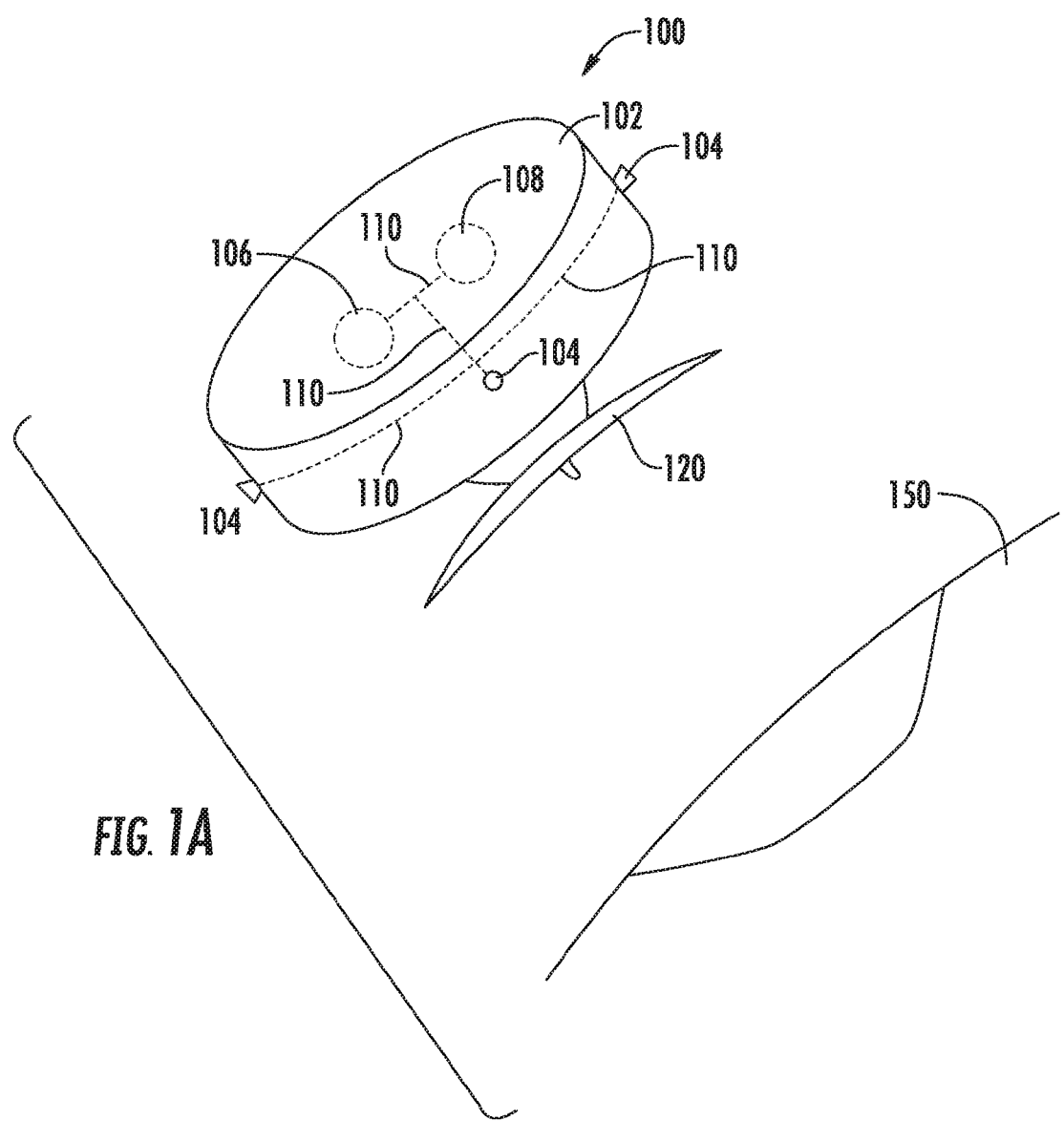
FIG. 1A is a perspective view of a satellite orbiting the earth, wherein certain systems of the satellite are depicted in a block diagram.

In the following, reference is made to aspects presented in this disclosure. However, the scope of the present disclosure is not limited to specific described aspects. Instead, any combination of the following features and elements, whether related to different aspects or not, is contemplated to implement and practice contemplated aspects. Furthermore, although aspects disclosed herein may achieve advantages over other possible solutions or over the prior art, whether or not a particular advantage is achieved by a given aspect is not limiting of the scope of the present disclosure. Thus, the following aspects, features, and advantages are merely illustrative and are not considered elements or limitations of the appended claims except where explicitly recited in a claim(s). Likewise, reference to "the invention" or "the disclosure" shall not be construed as a generalization of any inventive subject matter disclosed herein and shall not be considered to be an element or limitation of the appended claims except where explicitly recited in a claim(s).

Satellites use thrusters to correct their trajectories after they are placed into orbit. For example, a satellite in geostationary orbit uses thrusters to correct its position over the earth. As another example, a satellite orbiting at an altitude below geostationary orbit (e.g., low earth orbit or medium earth orbit) may use its thrusters to adjust its orbital trajectory.

Satellites also use thrusters to move out of their operating orbits (i.e., deorbit) when their service lives are over. For example, a satellite in geostationary orbit may use its thrusters to move to a higher orbit to free up space in the geostationary orbit ring for another satellite. As another example, a lower-orbiting satellite may use its thrusters to slow down and re-enter the earth's atmosphere (and thereby disintegrate). In many cases, the service life of a satellite is determined by the amount of thruster propellant remaining. When a satellite only has enough propellant remaining to perform the deorbit thrust maneuver (with a reserve for propellant mass uncertainties), the satellite has reached the end of its service life.

To maximize the service life of a satellite, the amount of propellant mass in a propellant storage volume (e.g., a propellant storage tank) is calculated while the satellite is in service to determine and/or predict when the amount of gaseous propellant is an amount for the deorbit thrust maneuver (plus a reserve). Traditionally, the amount of propellant is calculated using a bookkeeping method. The bookkeeping method uses a known starting quantity of propellant when the satellite is launched. Every time the satellite uses propellant by using its thrusters, the amount of propellant used is subtracted from the known starting quantity to result in a calculated quantity of propellant. A shortcoming with the bookkeeping method is that any errors in measurements of how much propellant was used are cumulative for each thrust application. For example, suppose that a mass flow sensor used on a satellite to measure the flow of propellant has an accuracy of plus or minus 0.01 kg. Now, suppose that over a period of time the satellite performs one hundred thrust operations, wherein each thrust operation is intended to use 0.1 kg of propellant. Based on the exemplary accuracy of the sensor, the satellite could have used as little as 9.0 kg of propellant or as much as 11.0 kg of propellant. Over one thousand thrust operations, the satellite could have used as little as 90 kg of propellant or as much as 110 kg of propellant. To be conservative, in such a scenario, satellite operators would assume that the satellite used 110 kg of propellant (to account for the cumulative measurement uncertainty) and plan for the deorbit thrust maneuver accordingly. However, in doing so, the satellite operators could give up significant remaining service life (e.g., if the satellite in fact had only used 90 kg of propellant, then the 20 kg of propellant would be unused).

The amount of propellant has also been calculated using the Pressure-Volume-Temperature (PVT) method, in which a density of a gaseous propellant is calculated based on the measured pressure and temperature of the gas under ideal gas law assumptions. The calculated density is then multiplied by a volume of the propellant storage volume (e.g., a propellant tank) to result in a calculated mass of the propellant in the tank. An ideal gas, among other things, is assumed to have linear compressibility, meaning that the density of the gas is linearly proportional to the pressure and/or temperature of the gas. As will be discussed in greater detail below, real gases used as propellants, such as xenon or gas mixtures, do not necessarily follow the ideal gas model, particularly at higher pressures and lower temperatures where intermolecular forces and molecular size become important. Therefore, the PVT method using ideal gas law properties results in an inaccurately calculated density. Modeling the density using equations of state also results in an inaccurate calculated density.

In aspects described herein, a more-accurate density of a gaseous propellant is calculated based on actual thermodynamic property data for the gaseous propellant, measured pressures of gaseous propellant, and measuring temperatures of gaseous propellant. Furthermore, a more-accurate volume of a propellant storage volume (in the exemplary aspects described below, a propellant tank or propellant tanks) is calculated based on a known empty volume of the tank and an expansion factor for the tank based on the measured pressure and, optionally, the measured temperature. A product of the more-accurate density and the more-accurate volume is calculated to determine a more-accurate gaseous mass in a propellant storage volume (e.g., propellant tank).

FIG. 1A illustrates a satellite 100 in orbit around the earth 150. The satellite 100 could be in low earth orbit, medium earth orbit, or geostationary orbit, for example. The satellite 100 includes a satellite body 102 that houses various internal components and also acts as a support structure for various instruments, such as a communications antenna 120. The satellite 100 includes thrusters 104 arranged around the satellite body 102. Gaseous propellant, such as xenon gas, is stored in propellant tanks 106 and 108 and can be supplied to the thrusters 104 via propellant feed lines 110.

Figure 1B:
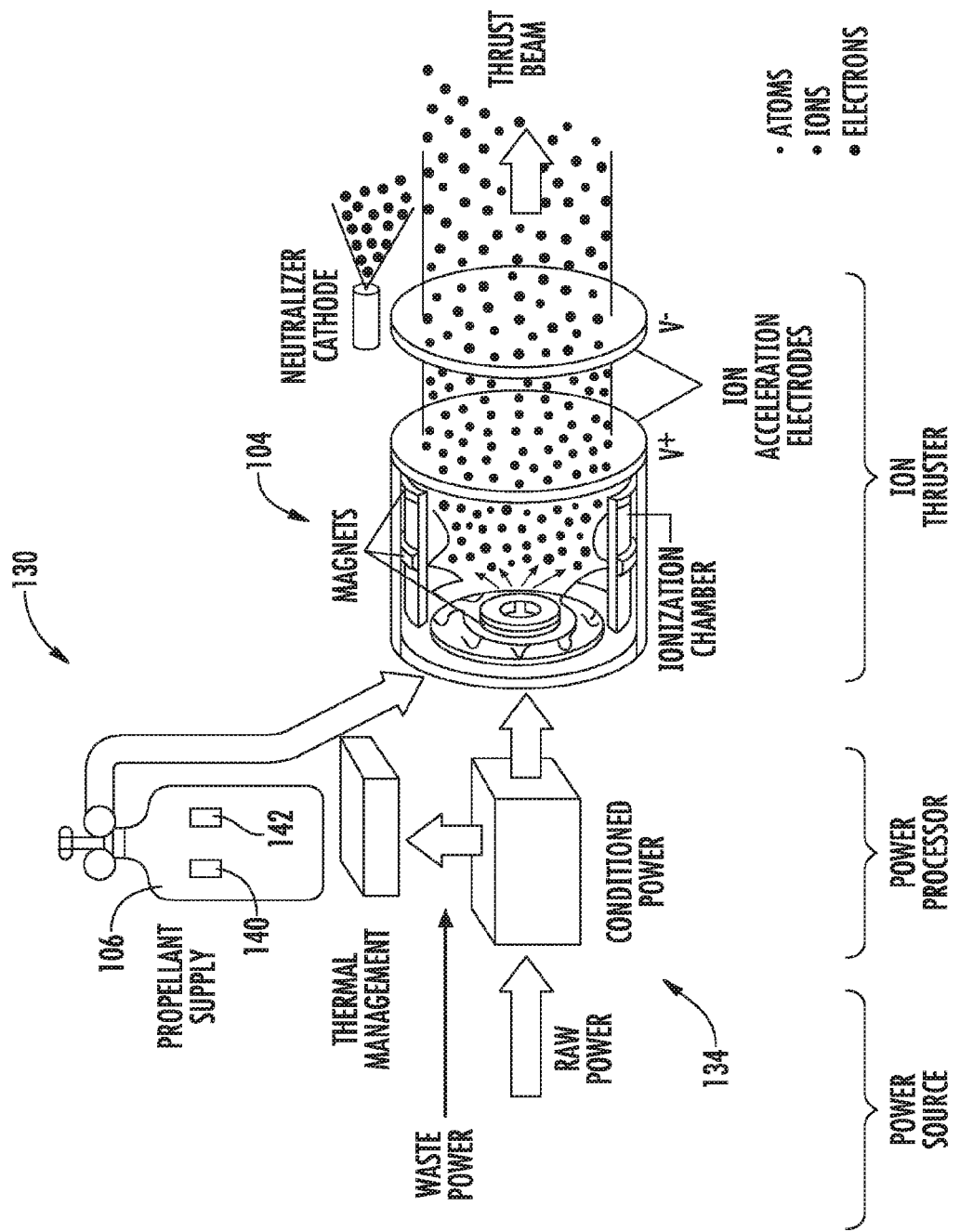
FIG. 1B is a block diagram depiction of a thruster system for use with a satellite.

FIG. 1B is a schematic view of a thruster arrangement 130 for a satellite, such as the satellite 100 shown in FIG. 1A. The thruster arrangement 130 includes the propellant tank 106 (the propellant tank 108 is not shown) and a thruster 104. In the exemplary thruster arrangement 130 shown in FIG. 1B, the thruster 104 is an ion thruster used in electric propulsion systems. The thruster arrangement 130 includes an electrical power supply 134 that supplies electrical voltages and currents to the ion thruster. In use, an amount of gaseous propellant from the propellant tank 106 is released to the thruster 104 and the electrical power supply 134 supplies power to the thruster 104. The electrical power ionizes the gaseous propellant, and the thruster 104, which is similarly charged, accelerates the ionized gaseous propellant to generate thrust. The propellant tank 106 can include one or more pressure transducers 140 therein, which measures pressure of the gaseous propellant in the propellant tank 106. The propellant tank 106 also includes one or more temperature sensors 142, which measures temperature of the gaseous propellant in the propellant tank 106.

Figure 2:
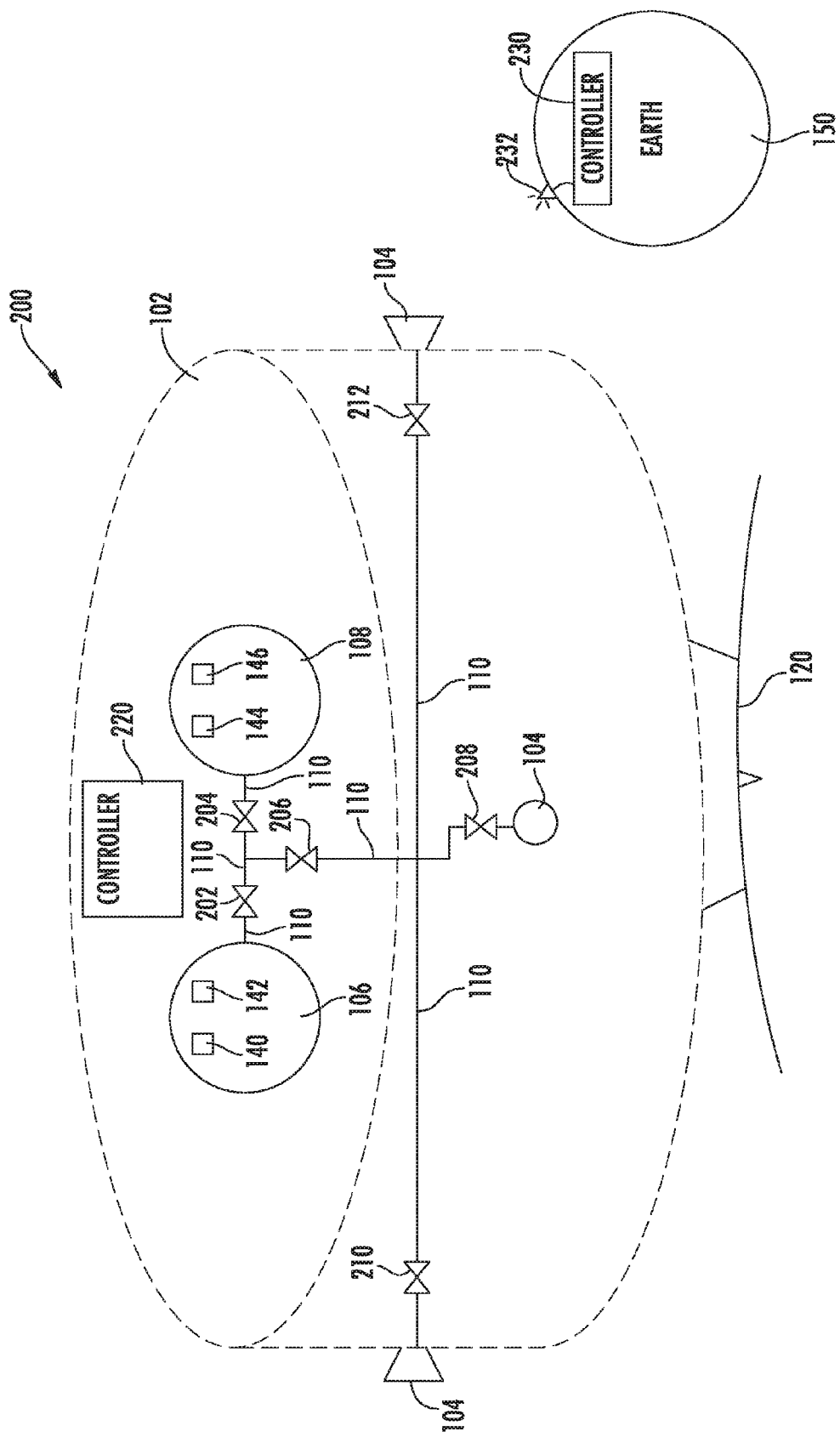
FIG. 2 is a side view of a satellite according to at least one aspect, wherein certain systems of the satellite are depicted in a block diagram.

FIG. 2 is a block diagram view of a satellite system 200 according to one aspect. The satellite system 200 includes the satellite body 102 with the thrusters 104 arranged there around. The satellite system 200 also includes the communications antenna 120 and could include other instruments, such as cameras and sensors. The satellite system 200 includes a first propellant tank 106 and a second propellant tank 108 arranged in or on the satellite body 102. The first propellant tank 106 includes a pressure transducer 140 that measures pressure of the gaseous propellant, such as xenon gas, in the first propellant tank 106 and a temperature sensor 142 that measures temperature of the gaseous propellant in the first propellant tank 106. The second propellant tank 108 includes a pressure transducer 144 that measures pressure of the gaseous propellant, such as xenon gas, in the second propellant tank 108 and the temperature sensor 146 that measures temperature of the gaseous propellant in the second propellant tank 108. The propellant tanks 106 and 108 are connected to the thrusters 104 via propellant feed lines 110.

Valves arranged along the propellant feed lines 110 can be selectively opened and closed by a controller 220 to control a flow of gaseous propellant from one or both of the propellant tanks 106 and 108 to the thrusters 104. For example, valves 202, 206, and 210 could be selectively opened to permit flow of gaseous propellant from the first propellant tank 106 to a first of the thrusters 104. As another example, valves 202, 206, and 208 could be selectively opened to permit flow of gaseous propellant from the first propellant tank 106 to a second of the thrusters 104. As another example, valves 202, 206, and 212 could be selectively opened to permit flow of gaseous propellant from the first propellant tank 106 to a third of the thrusters 104. As another example, valves 204, 206, and 210 could be selectively opened to permit flow of gaseous propellant from the second propellant tank 108 to the first of the thrusters 104. As another example, valves 204, 206, and 208 could be selectively opened to permit flow of gaseous propellant from the second propellant tank 108 to the second of the thrusters 104. As another example, valves 204, 206, and 212 could be selectively opened to permit flow of gaseous propellant from the second propellant tank 108 to the third of the thrusters 104. In various aspects, valves 202 and 204 could be selectively opened (while the valve 206 is closed) to permit flow of the gaseous propellant from the first propellant tank 106 to the second propellant tank 108 or from the second propellant tank 108 to the first propellant tank 106.

The satellite system 200 can be in communication with the earth 150 via the communications antenna 120. For example, the communications antenna 120 could transmit data to a transceiver 232 on the earth 150 and receive data from the transceiver 232. The transceiver 232 could be in communication with a controller 230 on the earth 150. As will be discussed in greater detail below, the controller 220 on board the satellite system 200 and/or the controller 230 on the earth 150 can be used to calculate a mass of the propellant in the propellant tanks 106 and 108.

Figure 3:
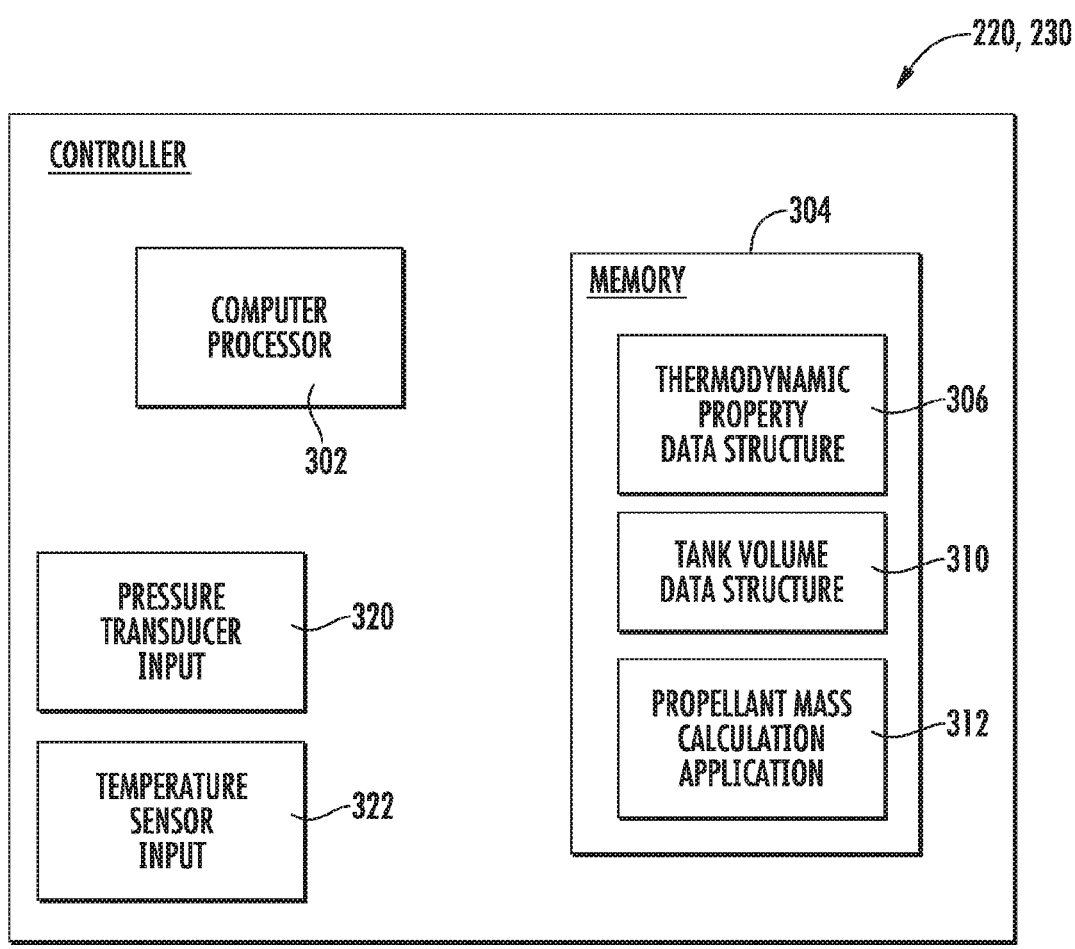
FIG. 3 is a block diagram of a controller for use onboard a satellite and/or at a ground control station for calculating a mass of propellant in a propellant tank.

FIG. 3 is a block diagram of a controller according to at least one aspect, such as the controller 220 on board the satellite system 200 and/or the controller 230 on the earth 150 depicted in FIG. 2, that can calculate a mass of propellant in the propellant tanks 106 and 108 of the satellite system 200. The controller 220 or 230 includes a pressure transducer input 320 operable to receive pressure data from pressure transducers, such as the pressure transducer 140 on the first propellant tank 106 and/or the pressure transducer 144 on the second propellant tank 108. The controller 220 or 230 also includes a temperature sensor input 322 operable to receive temperature data from temperature sensors, such as the temperature sensor 142 on the first propellant tank 106 and/or the temperature sensor 146 on the second propellant tank 108. The controller 220 or 230 also includes a computer processor 302 and computer memory 304. The computer memory 304 stores a thermodynamic property data structure 306 for the gaseous propellant stored in the propellant tanks 106 and 108. For example, the thermodynamic property data structure 306 could include data from the National Institute of Standards and Technology (NIST) Reference Fluid Thermodynamic and Transport Properties Database (version 9.1), the entire contents of which are incorporated by reference herein. The NIST database provides, inter alia, look-up tables of pressure, temperature, and density relationships for various gases or gas mixtures. The computer memory 304 also stores a propellant tank volume data structure 310 for the propellant tanks 106 and 108. The propellant tank volume data structure 310 includes a measured volume of each of the propellant tanks 106 and 108 at a nominal pressure (e.g., such as zero gauge pressure, wherein the gauge pressure is the difference in pressure between the pressure in the propellant tank and the ambient pressure of the atmosphere outside of the tank). The propellant tank volume data structure 310 also includes measured volumes of each of the propellant tanks 106 and 108 at other pressures, such as for a range of gauge pressures between zero megapascals (MPa) and twelve MPa. The propellant tank volume data structure 310 could include absolute volumes of each of the pressure tanks 106 and 108 at the different pressures and/or could include changes in volume from the nominal volume (expressed as a percentage or as a volume) at the different pressures. Optionally, the propellant tank volume data structure 310 could also include measured volumes of each of the propellant tanks 106 and 108 at different temperatures of the tank structure to account for thermal effects on the volume of the propellant tank (e.g., due to thermal variations caused by tank and/or satellite heaters). In such instances, the temperature sensors (e.g., the temperature sensors 142 and/or 146) could include a first temperature sensor measuring a temperature of the gas in the propellant tank and a second temperature sensor measuring a temperature of the respective propellant tank structures. The propellant tank volume data structure 310 could include absolute volumes of each of the pressure tanks 106 and 108 at the different temperatures and/or could include changes in volume from the nominal volume (expressed as a percentage or as a volume) at the different temperatures. In various aspects in which the propellant tanks are constructed to high tolerances such that tank-to-tank variability is minimal or insubstantial, the propellant tank volume data structure 310 could include a nominal tank volume and volume variances for different pressures (and, optionally, different temperatures) for a representative propellant tank. The tank volume data for the representative propellant tank is used to calculate the volume of the propellant tanks (e.g., the propellant tanks 106 and 108) of the satellite, based on measured pressures and, optionally, measured temperatures.

The computer memory 304 can also store a propellant mass calculation application 312 that can be executed on the computer processor 302 to calculate a mass of propellant in each of the propellant tanks 106 and 108. The mass of gaseous propellant in a propellant tank is equal to the density of the gaseous propellant (where in the density is expressed as a mass per unit volume, such as grams per cubic centimeter) multiplied by the volume of the propellant tank storing the gaseous propellant. Thus, to calculate the mass of gaseous propellant in a propellant tank, a density of the gaseous propellant in the propellant tank must be calculated and a volume of the propellant tank must be determined or calculated.

The controller 220 or 230 can include outputs to communicate with the valves 202, 204, 206, 208, 210, and 212 and the thrusters 104. The controller 220 and 230 is operable to output thrust control commands via the outputs that direct propellant from one or more of the propellant tanks 106 and 106 to appropriate thrusters to steer the satellite body 102.

Figure 4A:
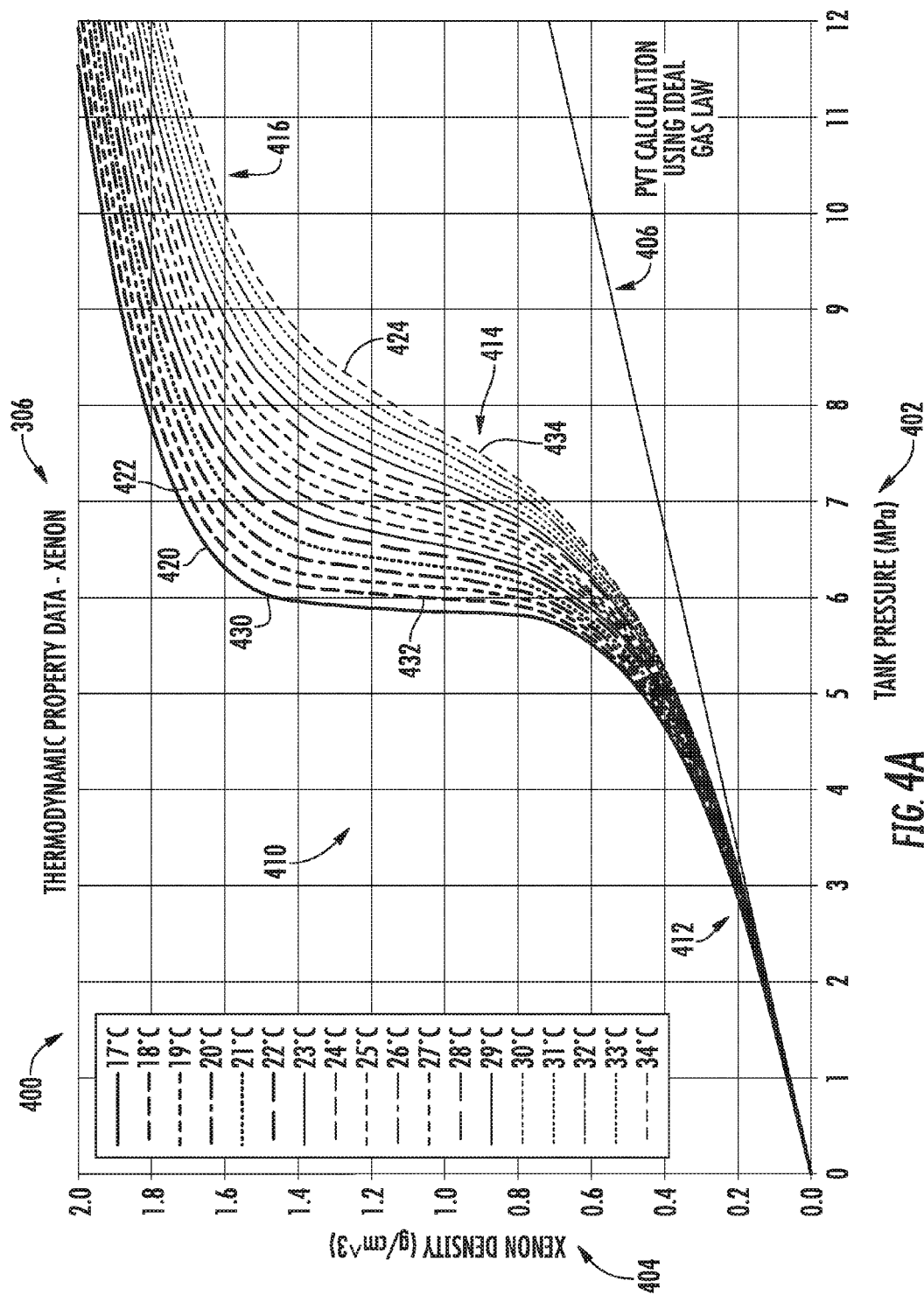
FIG. 4A is a graphical representation of density data for xenon gas at various pressures and temperatures and also a graphical representation of density data for an ideal gas.

FIG. 4A is a graphical depiction 400 of thermodynamic property data for xenon gas that could be included in the thermodynamic property data structure 306. The graphical depiction 400 includes tank pressures on the horizontal axis 402 and a calculated density of the xenon gas on the vertical axis 404. In the graphical depiction 400, the thermodynamic property data is represented as a plurality of density curves 410 for xenon gas at a range of temperatures between 17° C. and 34° C. in 1° C. increments. For example, the density curve 420 for 17° C. is the leftmost curve on the graphical depiction 400, the density curve 422 for 18° C. is the next leftmost curve on the graphical depiction 400, and the density curve 424 for 34° C. is the rightmost curve on the graphical depiction 400.

As illustrated by the graphical depiction 400, xenon gas has a non-linear relationship between pressure, temperature, and density. The xenon gas has a substantially linear relationship between pressure, temperature, and density in a first compressible region 412 between zero MPa and approximately 4 MPa. The xenon gas also has a substantially linear relationship between pressure, temperature, and density in a second compressible region 416 at pressures above approximately 10 MPa. However, in a super compressible region 414 between approximately 4 MPa and 10 MPa, the xenon gas is more compressible, meaning the xenon gas has a larger increase in density for a given pressure change in the super compressible region 414 than in the compressible regions 412 and 416. For the purposes of comparison, the graphical depiction 400 also illustrates the linear approximation 406 for the relationship between pressure and density for xenon gas, according to the ideal gas law calculation. As shown, at low pressures (e.g., pressures below approximately 2.5 MPa) in the first compressible region 412, the density of the xenon gas calculated by the ideal gas law method is close to the density from the thermodynamic property data (represented by the density curves 410). However, at higher pressures approaching the super compressible region 414, the density calculated by the ideal gas law method substantially varies from the data in the thermodynamic property data structure 306.

To determine a density of xenon gas in a propellant tank, a pressure and temperature of the xenon gas in the propellant tank is measured. For example, with reference to FIG. 2, the pressure transducer 140 and the temperature sensor 142 in the first propellant tank 106 could measure the pressure and temperature in the first propellant tank 106. As another example, the pressure transducer 144 and the temperature sensor 146 in the second propellant tank 108 could measure the pressure and temperature in the second propellant tank 108. The measured pressure and temperature could be transmitted to the controller 220 or 230 (via the communications antenna 120 on the satellite system 200 and the transceiver 232). The propellant mass calculation application 312, executing on the computer processor 302, could perform a table look-up function or query on the thermodynamic property data structure 306 to determine a density of the xenon gas in the propellant tank based on the measured pressure and temperature. For example, with reference to FIG. 4A, suppose that the measured pressure of the xenon gas in the propellant tank 106 is 6 MPa and the measured temperature of the xenon gas is 17° C. A point (indicated by reference numeral 430) on the graphical depiction 400 corresponding to 6 MPa and 17° C. corresponds to a xenon density of approximately 1.48 g/cm$^3$. As another example, suppose that the measured pressure of the xenon gas in the propellant tank 106 is 6 MPa and the measured temperature of the xenon gas is 18° C. A point (indicated by reference 432) on the graphical depiction 400 corresponding to 6 MPa and 18° C. corresponds to a xenon density of approximately 1.05 g/cm$^3$. In these two examples, a measurement difference of 1° C. could result in a change of calculated density of 0.43 g/cm$^3$. As another example, suppose that the measured pressure of the xenon gas in the propellant tank 106 is 7.5 MPa and the measured temperature of the xenon gas is 34° C. A point (indicated by reference 434) on the graphical depiction 400 corresponding to 7.5 MPa and 34° C. corresponds to a xenon density of approximately 0.90 g/cm$^3$.

Figure 5:
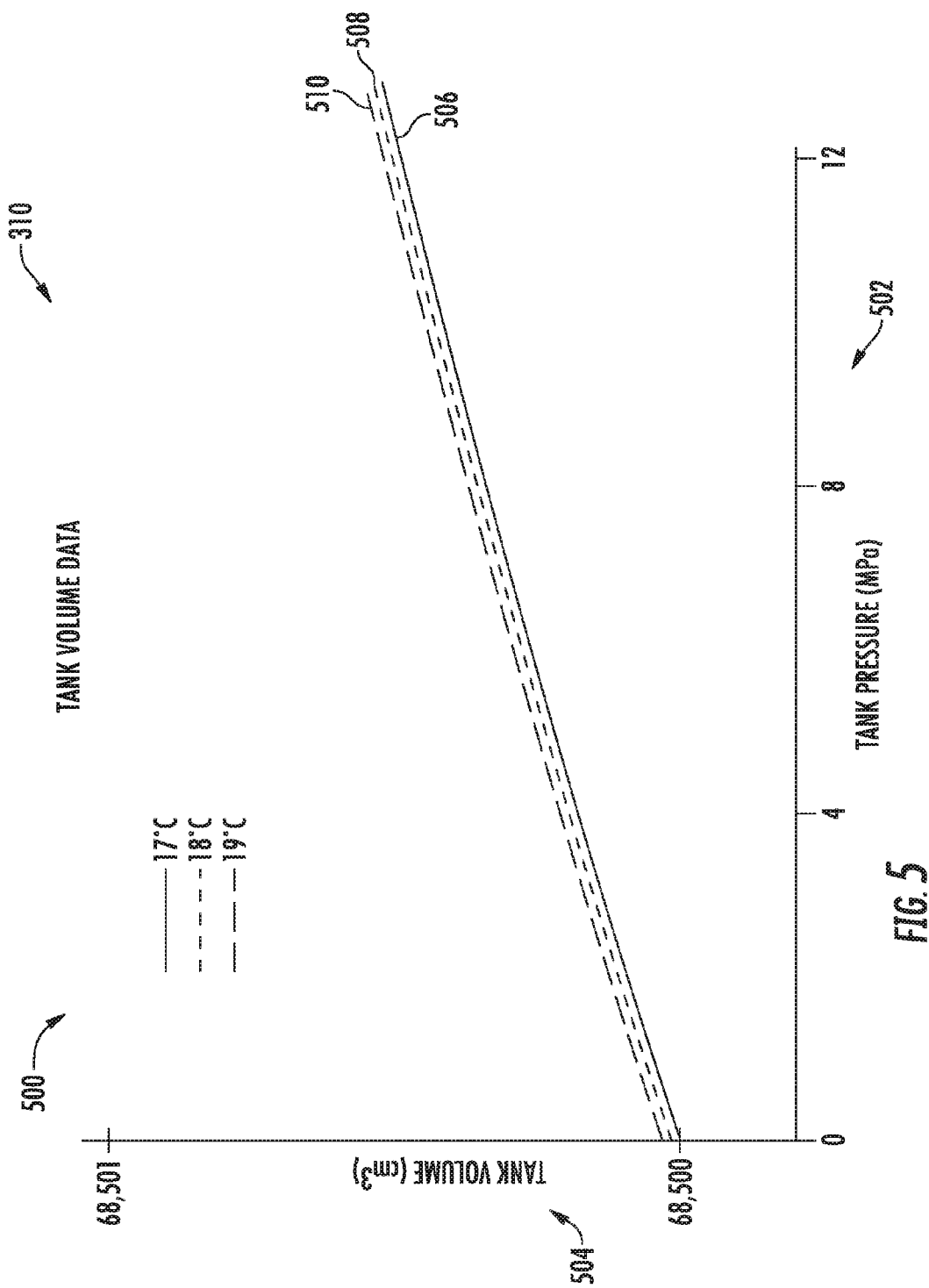
FIG. 5 is a graphical representation of volume of a propellant tank at various pressures and temperatures.

FIG. 5 is a graphical depiction 500 of exemplary tank volume data of a propellant tank (e.g., the propellant tank 106 or the propellant tank 108 or a representative propellant tank). The graphical depiction 500 includes pressure of propellant in the tank along the horizontal axis 502 (in MPa) and a tank volume along the vertical axis 504 (in cubic centimeters). In the graphical depiction 500, the exemplary propellant tank has a nominal volume (a volume when the pressure inside the propellant tank is equal to a pressure outside of the pressure tank) of 68,500 cm$^3$ when a temperature of the gas in the propellant tank (and the temperature of the tank) are equal to 17° C. As the pressure in the tank increases, the propellant tank expands. As a result, the volume of the propellant tank increases. The line 506 on the graphical depiction 500 represents data for volumes of the tank at various pressures at 17° C. The line 508 on the graphical depiction 500 represents data for volumes of the tank at various pressures at 18° C. The line 510 on the graphical depiction 500 represents data for volumes of the tank at various pressures at 19° C. Data for other temperatures could also be included, but is omitted herein for brevity and clarity. To simplify the computer processing, the lines 506, 508, and 510 corresponding to different fixed temperatures could be statistically curve-fitted to yield an equation of tank volume for each of the propellant tanks 106 and 108 (or for a representative tank) as a function of tank pressure.

As shown in FIG. 5, temperature changes can have a relatively small effect on the volume of the propellant tank. In the environment of a satellite, such as the satellite system 200 depicted in FIG. 2, in which the propellant tanks may be insulated, the temperature of the propellant tank may vary by only a few degrees, such as the range of temperatures between 17° C. and 34° C. shown in FIG. 4A. In such circumstances, variations in volume of the propellant tank based on temperature may be ignored to simplify a calculation of the volume of the propellant tank, such as using a statistical curve-fit for a propellant tank of volume as a function of pressure. In other circumstances, such as when larger temperature variations may occur or when increased accuracy is required, such temperature effects on the volume can be included in the calculation of the volume of the propellant tank.

As discussed above, the data for the propellant tank volume data structure 310 can be gathered through ground tests performed on a propellant tank in a laboratory or test environment. The tests could be performed on each propellant tank individually such that the propellant tank volume data structure 310 is specific to a particular propellant tank. Alternatively, the tests could be performed on a representative propellant tank, and the propellant tank volume data structure 310 could include data for the representative propellant tank that is applied to all of the propellant tanks.

To calculate a volume of the propellant tank while in use (e.g., while the satellite system 200 is in orbit), the propellant mass calculation application 312, being executed on the computer processor 302, performs a look-up function or query on the propellant tank volume data structure 310 to determine a volume of the propellant tank. The look-up function or query could be based on the pressure of the propellant in the propellant tank and, optionally as discussed above, on the temperature of the propellant in the propellant tank. Optionally, tank volume could be based on measurements from stress or strain sensors mounted to the surface of the tank surfaces. Similar to the determination of the density of the gaseous propellant, discussed above with reference to FIG. 4A, the propellant mass calculation application 312 can identify the tank volume corresponding to the measured pressure (and optionally the measured temperature) from the tank volume data structure 310.

Figure 4B:
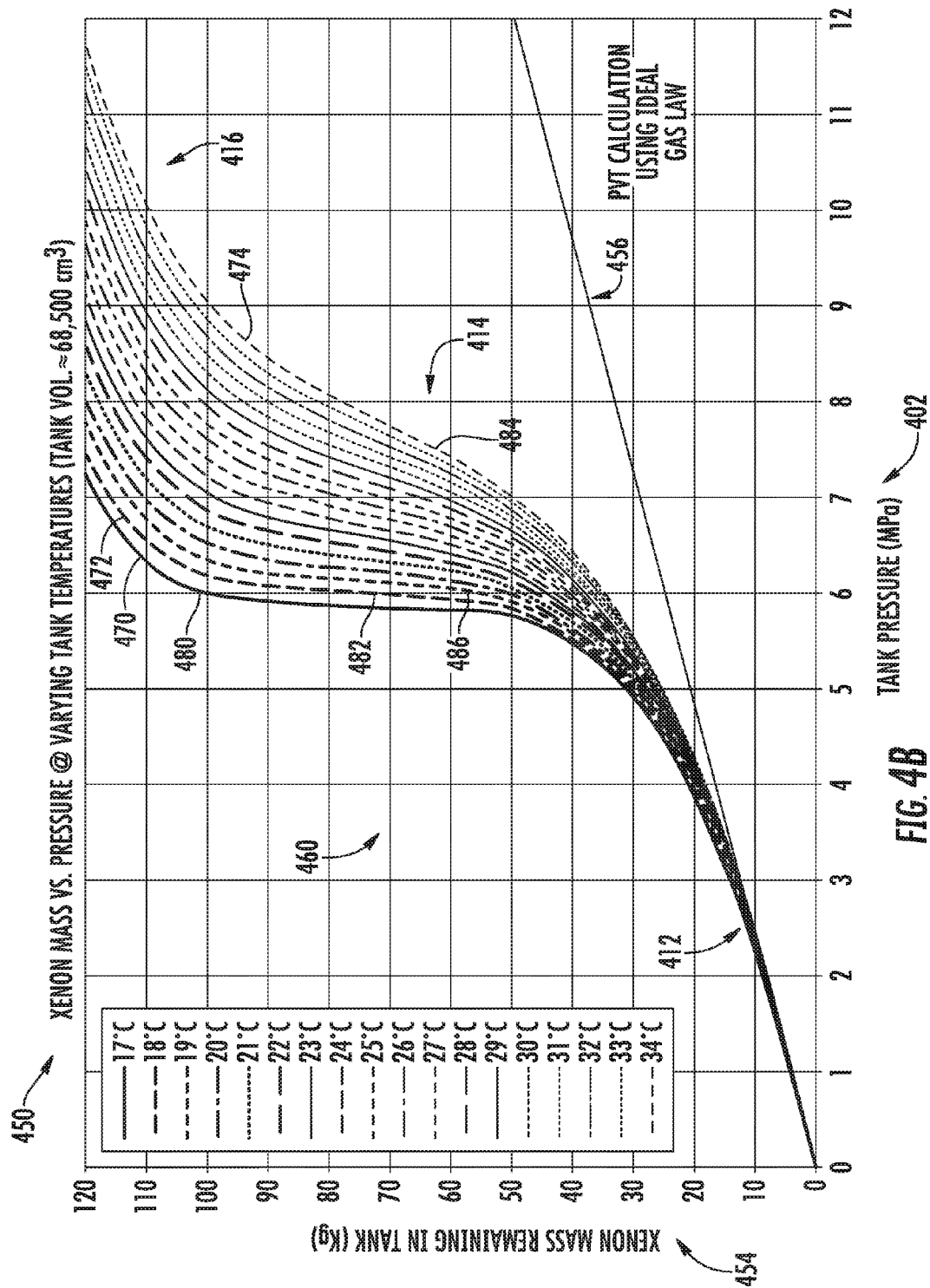
FIG. 4B is a graphical representation of mass data for xenon in a propellant tank having a nominal volume of approximately 68,500 $cm^3$, based on the density data shown in FIG. 4A.

As discussed above, after the density of the gaseous propellant has been calculated, the calculated density can be multiplied by a volume of a propellant tank to determine a calculated mass of the propellant in the tank. FIG. 4B illustrates a graphical depiction 450 of masses of gaseous xenon in a propellant tank having a nominal volume of approximately 68,500 cm$^3$ for different pressures and temperatures. In FIG. 4B, the calculated volume of the propellant tank used for calculating a mass of propellant varies with pressure. As discussed above, in various aspects, the calculated volume of the pressure tank could vary based on pressure and temperature. Since the density for xenon gas varies non-linearly with pressure, the mass of xenon gas similarly varies in a non-linear manner. In the graphical depiction 450, the calculated masses of xenon are represented as a plurality of mass curves 460 for xenon gas in the propellant tank at a range of temperatures between 17° C. and 34° C. in 1° C. increments. The mass curve 470 for 17° C. is the leftmost curve on the graphical depiction 450, the mass 472 for 18° C. is the next leftmost curve on the graphical depiction 450, and the mass curve 474 for 34° C. is the rightmost curve on the graphical depiction 450.

To calculate a mass of xenon gas in a propellant tank, the propellant mass calculation application 312, executing on the computer processor 302, multiplies the density determined based on the measured pressure and temperature (described above with reference to FIG. 4A) by the volume of the propellant tank. For example, referencing FIGS. 4A and 4B, as discussed above, if that the measured pressure of the xenon gas in the propellant tank 106 is 6 MPa and the measured temperature of the xenon gas is 17° C., then the density of the xenon is approximately 1.48 g/cm$^3$. In this example and the following examples, the nominal volume of the propellant tank is assumed to be 68,500 cm$^3$ regardless of the pressure and temperature in the propellant tank. Multiplying the density of 1.48 g/cm$^3$ by the nominal volume of 68,500 cm$^3$ results in a calculated mass of approximately 101 kg of xenon. A point on the graphical depiction 450 of FIG. 4B (indicated by reference numeral 480) corresponding to 6 MPa and 17° C. corresponds to a xenon mass of approximately 101 kg. As another example, as discussed above, if the measured pressure of the xenon gas in the propellant tank 106 is 6 MPa and the measured temperature of the xenon gas is 18° C. then the density of the xenon is approximately 1.05 g/cm$^3$. Multiplying the density of 1.05 g/cm$^3$ by the nominal volume of 68,500 cm$^3$ results in a calculated mass of approximately 72 kg of xenon. A point on the graphical depiction 450 of FIG. 4B (indicated by reference numeral 482) corresponding to 6.0 MPa and 18° C. corresponds to a xenon mass of approximately 72 kg. As another example, as discussed above, if that the measured pressure of the xenon gas in the propellant tank 106 is 7.5 MPa and the measured temperature of the xenon gas is 34° C. then the density of the xenon is approximately 0.90 g/cm$^3$. Multiplying the density of 0.90 g/cm$^3$ by the nominal volume of 68,500 cm$^3$ results in a calculated mass of approximately 62 kg of xenon. A point on the graphical depiction 450 of FIG. 4B (indicated by reference numeral 484) corresponding to 7.5 MPa and 34° C. corresponds to a xenon mass of approximately 62 kg.

Referring primarily to FIG. 4B, measurement errors by the pressure transducers and/or temperature transducers can result in significant errors in the calculated density and calculated mass of propellant in a propellant tank. For example, at a pressure of 6 MPa, the mass of xenon in the exemplary propellant tank (with an approximate volume of 68,500 cm$^3$) would be approximately 101 kg if the temperature is 17° C. (as indicated by reference numeral 480) and would be approximately 72 kg if the temperature is 18° C. (as indicated by reference numeral 482). Consequently, the calculation of propellant in the exemplary propellant tank could be off by 29 kg if the measured temperature has an error of plus or minus 1° C. For example, a temperature sensor used in the propellant tank, such as the temperature sensor 142 in the propellant tank 106 or the temperature sensor 146 in the propellant tank 108 shown in FIG. 2, could have an accuracy of plus or minus 1° C. Thus, a measured temperature of 18° C. could mean that the actual temperature is as low as 17° C. or as high as 19° C. Referring to FIG. 4B again, such a measurement range would result in a calculated mass of propellant in the exemplary propellant tank as high as 101 kg (as indicated by reference numeral 480) or as low as 58 kg (as indicated by reference numeral 486). One strategy to minimize the impacts of measurement errors is to operate the propellant tanks as far away as practical from the known critical conditions of the propellant gas (e.g., approximately 5.84 MPA and 16.7° C. for xenon). Referring to FIG. 4B, at a temperature of 17° C. and a pressure of 5.85 MPa, the calculated mass changes substantially for a small change in measured pressure. For example, the calculated mass is approximately 58 kg at a measured pressure of 5.8 MPa and is approximately 88 kg at a measured pressure of 5.9 MPa. Consequently, the calculation of propellant in the exemplary propellant tank could be off by only 8 kg if the measured temperature has an error of plus or minus 1° C. By operating the propellant tanks at pressures and/or temperatures away from the critical conditions (e.g., at a measured pressure of 7.5 MPa), the mass calculations can be significantly less sensitive to changes in measured pressure and measured temperature. For example, still referring to FIG. 4B, at a measured pressure of 7.5 MPa and a measured temperature of 33° C., the calculated mass of xenon in the propellant tank is approximately 65 kg. If the error in the temperature sensor means that the measured temperature of 33° C. could be as low as 32° C. or as high as 34° C., then the calculated mass could be between approximately 69 kg and 62 kg; a much smaller error range than discussed above.

Also, if the error in the pressure sensor means that the measured pressure of 7.5 MPa could be as low as 7.4 MPa or as high as 7.6 MPa, then the calculated mass could be between 60 kg (at a temperature of 34° C.) and 72 kg (at a temperature of 32° C.); also a much smaller error range than discussed above.

Figure 6:
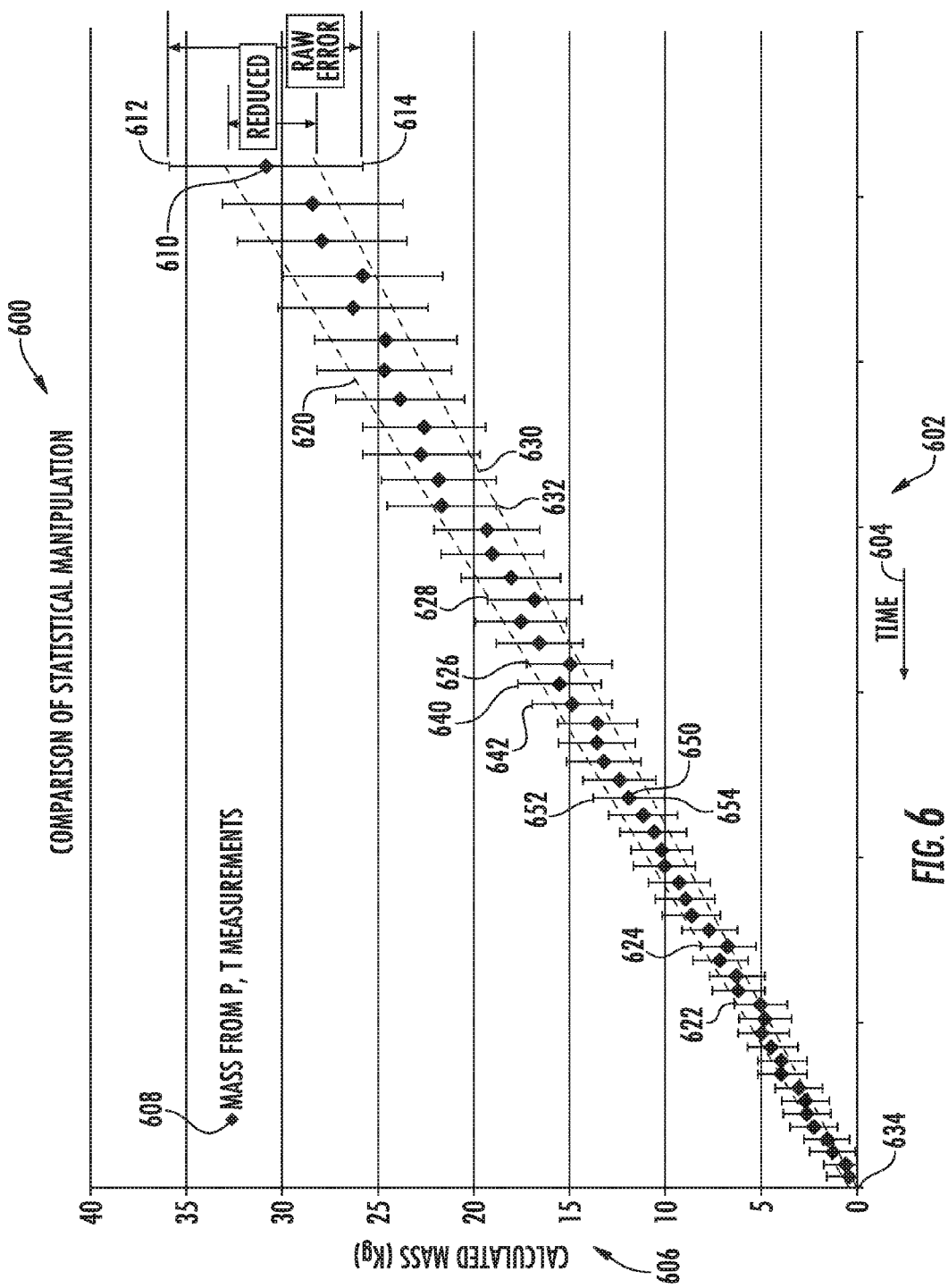
FIG. 6 is a graphical representation of various calculated mass data points with respective error bars representing inherent accuracy limitations of pressure transducers and temperature sensors, and also showing reduced error lines based on trends in the calculated mass data points and respective error bars.

To reduce the error in the mass calculation caused by inherent accuracy limitations of the pressure transducers and/or the temperature sensors, the propellant mass calculation application 312, executing on the computer processor 302, can perform various statistical analyses, statistical operations, mathematical operations, and/or data analysis on the measured pressures and/or temperatures output by the pressure transducers and/or the temperature sensors to reduce the level of error. FIG. 6 is a graphical depiction 600 of exemplary calculated masses 608 over time. The graphical depiction 600 includes time on a horizontal axis 602, wherein time advances in the direction of arrow 604, and calculated mass 606 on the vertical axis. Each calculated mass 608 is the result of the propellant mass calculation application 312, executing on the computer processor 302, calculating a density of the propellant and a volume of the propellant tank based on the measured pressure and temperature of the propellant, and calculating a mass of the propellant by multiplying the calculated density by the calculated volume, described above with reference to FIGS. 4A and 4B.

Each calculated mass 608 could be the result of a single measurement of pressure and temperature from pressure transducers and temperature sensors or could be the result of many measurements of pressure and temperature. For example, with reference to the propellant tank 106 and in FIG. 2, the pressure transducer 140 could measure pressure of the propellant in the propellant tank 106 once every second, once per minute, or at some other frequency. The measured pressures over a time interval, such as over an hour, over a day, or over a week, could be averaged to eliminate pressure fluctuations due to daily or seasonal temperature variations, effects due to periodic thermal cycling of the propellant tank heaters, sensor lag or drift with time, bit transmission errors, or other measurement errors. Similarly, the temperature sensor 142 could measure temperature of the propellant in the propellant tank 106 once every second, once every minute, or at some other frequency. The measured temperatures over the time interval could also be averaged to eliminate various measurement errors, similar to the effects mentioned above for pressure variations. Each calculated mass 608 has an associated raw error. For example, the calculated mass 610 (a calculated mass of approximately 31 kg) has an associated raw error such that the calculated mass could be as high as approximately 36 kg (as indicated by an outer limit of error bar 612) or as low as 26 kg (as indicated by an outer limit of error bar 614). The raw errors are the result of the inherent accuracy limitations of the pressure transducers and temperature sensors at particular operating conditions, as discussed above. Such raw errors could be unsuitable for calculating a mass of propellant in a propellant tank.

To reduce the raw error in the mass calculations, the propellant mass calculation application 312, executing on the computer processor 302, could perform data or statistical analyses on the measured data. For example, FIG. 6 illustrates a trend of calculated mass over time. As time progresses and propellant is used to perform thrust operations (or effects due to leaks or losses from the system), the calculated mass decreases. This trend in calculated mass over time using statistical methods can be used to place reduced error lines 620 and 630 through the data. The reduced error lines 620 and 630 are placed on the graphical depiction such that each error line 620 and 630 touches an outer limit of at least one error bar and such that each error line 620 and 630 is between the outer limits of remaining error bars and the calculated masses 608. For example, the reduced error line 620 (i.e., the high mass error line) is placed on the graphical depiction 600 such that the reduced error line 620 touches or is close to the outer limits of error bars 622, 624, 626, and 628. Furthermore, none of the remaining high mass error bars have outer limits that are closer to the respective calculated masses 608 than the reduced error line 620. Similarly, the reduced error line 630 is placed on the graphical depiction 600 such that the reduced error line 630 touches or as close to the outer limits of error bar 632. In this instance, another point of the reduced error line 630 passes through an origin point 634 (i.e., a point in time on the horizontal axis 602) at which the mass of propellant is expected to be zero) of the graphical depiction 600. Again, none of the low mass error bars have outer limits that are closer to the respective calculated masses 608 than the reduced error line 630. The propellant mass calculation application 312, executing on the computer processor 302, could perform a mathematical and/or statistical best fit on outer limits of the error bars for the calculated masses 608 to place the reduced error lines 620 and 630 on the graphical depiction 600.

To explain the reasoning behind the reduced error lines 620 and 630, consider the error bar 626 and the error bars 640 and 642 for the subsequent two calculated masses 608. The outer limit of the error bar 626, touched by the reduced error line 620, represents the maximum possible mass at that time because it represents the calculated mass based on the measured values plus the maximum errors from the pressure transducers and temperature sensors. The next error bar 640 suggests that the maximum calculated mass could be as high as 18 kg. However, unless propellant was transferred to the tank (discussed in greater detail below), the propellant tank did not gain propellant. Thus, portions of the error bar 640 higher than 17.0 kg could be ignored. The reduced error lines identify a trend in the maximum and minimum known masses, based on points where the maximum error is at a low end of a range of errors. Continuing the example above, the reduced error line 620 indicates a trending maximum error range such that for the error bar 640, portions of the error bar 640 above approximately 16.5 kg can be ignored. Similarly, for the next error bar 642, portions of the error bar 642 above 16.0 kg can be ignored.

The reduced error lines 620 and 630 can be applied to future data points to reduce the error in the sensor readings. Continuing the example above, in which the calculated mass 610 is approximately 31 kg and the outer limits of the error bars 612 and 614 results in a possible range between approximately 36 kg and 26 kg, applying the reduced error lines 620 and 630 would reduce the range to between approximately 33 kg and 28 kg, respectively. As another example, consider the calculated mass 650 (approximately 12 kg) with outer limits of error bars 652 and 654 that resulted in a possible range between approximately 14 kg and 10 kg. Applying the reduced error line 620 and 630 would reduce the range to between approximately 13 kg and 11 kg, respectively.

In the graphical depiction 600 illustrated in FIG. 6, the calculated masses are shown over a period of time from when there is approximately 30 kg of propellant to a time when there is approximately 0 kg of propellant. In various aspects, the reduced error lines could be calculated based on calculated masses 608 over a relatively short interval of time, such as over several hours, several days, several weeks, several months, or several years. In various other aspects, the reduced error lines could be calculated based on calculated masses 608 over a relatively short interval of time defined by a change to the calculated mass of the propellant. For example, the reduced error lines could be calculated based on calculated masses 608 for the last 1 kg change of calculated mass, the last 5 kg change of calculated mass, etc.

Figure 7:
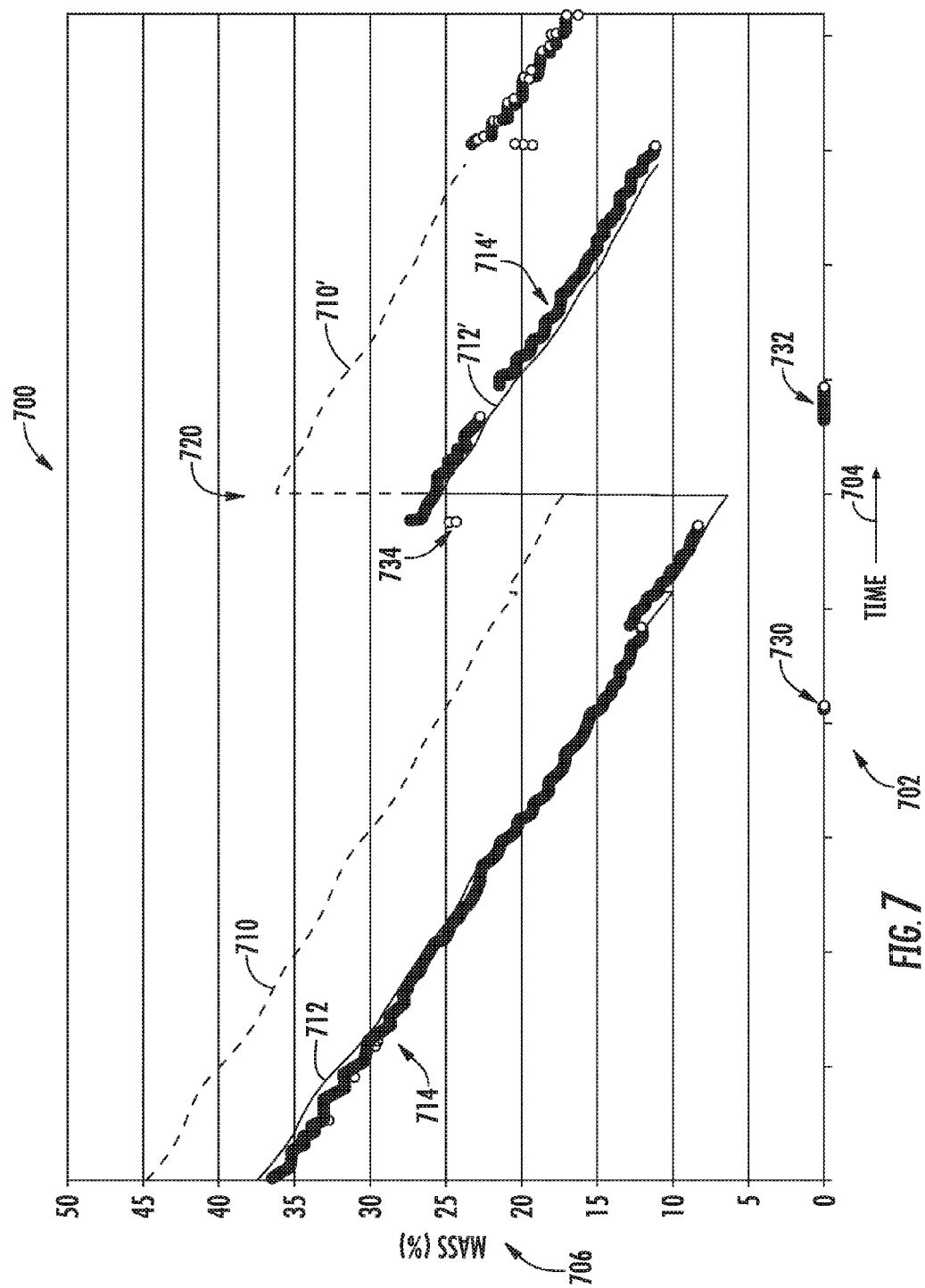
FIG. 7 is a graphical representation of calculated mass of propellant in a propellant tank according to a standard bookkeeping method, a bookkeeping method that accounts for losses, and a process based on calculating the volume of a propellant tank and a density of the propellant in the propellant tank.

FIG. 7 illustrates a graphical depiction 700 of calculated masses for a propellant storage volume (e.g., a propellant tank) according to the processes described above with reference to FIGS. 3, 4A, 4B, 5, and 6 and according to bookkeeping methods. The graphical depiction 700 includes time on the horizontal axis 702, with time advancing in the direction of arrow 704. The graphical depiction 700 includes a calculated mass of propellant in a propellant storage volume as a percentage of a starting mass on a vertical axis 706. As shown according to several different methods, discussed below, the total mass of propellant in the propellant storage volume generally decreases over time due to propellant usage, leaks, and/or losses. As discussed above, the bookkeeping method calculates an amount of propellant by subtracting every known use of the propellant from a known starting quantity of propellant. FIG. 7 illustrates a broken line 710 that represents a standard bookkeeping method that uses a simplified accounting methodology that ignores cumulative losses, such as leaks, startup losses, and shutdown losses. FIG. 7 also illustrates a solid line 712 that represents a bookkeeping method that accounts for such cumulative losses, resulting in a lower calculated mass of propellant. As shown in FIG. 7, calculated masses 714, calculated according to the processes described above with reference to FIGS. 3, 4A, 4B, 5, and 6 may generally match the bookkeeping method fairly well. As mentioned previously, the propellant gauging methods will eventually become more accurate over time than standard bookkeeping methods, since bookkeeping errors propagate and increase with time. In the event there is a discrepancy between the calculated masses, such as at points 730, 732, and 734, an alert could be generated to prompt an administrator for the satellite to perform diagnostic tests on the satellite system 200.

The graphical depiction 700 depicts a sharp increase in calculated mass in the propellant storage volume at the time indicated by the arrow 720. Referring again to FIG. 2 in various aspects, a satellite system 200 can include multiple propellant storage volumes, such as propellant tank 106 and propellant tank 108. In such aspects, propellant from one propellant storage volume could be transferred to the other propellant storage volume. For example, the controller 220 on board the satellite system 200 could close the valve 206 to isolate the propellant tanks 106 and 108 from the thrusters 104. Thereafter, the controller 220 could open the valves 202 and 204 to transfer propellant from one of the propellant tanks (e.g., propellant tank 106) to the other propellant tank (e.g., propellant tank 108). For example, the controller 220 could primarily draw propellant from the second propellant tank 108 to power the thrusters 104, reserving the propellant in the first propellant tank 108 for backup and/or emergency purposes. In the event the mass of the propellant in the second propellant tank 108 drops below a threshold level, propellant from the first propellant tank 106 could be transferred to the second propellant tank 108. In various other aspects, masses of propellants in the propellant tanks could be managed by the controller 220 and/or the controller 230 by maintaining the pressure and temperature in the propellant storage volumes away from the critical conditions, discussed above. For example, in one particular aspect, the process described above with reference to FIGS. 2, 3, 4A, 4B, 5, and 6 may be the most accurate in a particular range of masses, such as in a range from above approximately 90 kg or a range below approximately 35 kg. In such an exemplary aspect, the controller 220 could transfer propellant from the first propellant tank 160 to the second propellant tank 108 upon the calculated mass of propellant in the second propellant tank 108 dropping below 40 kg, 35 kg, or a different predetermined threshold mass, depending on the rate of propellant depletion with time.

Referring again to FIG. 7, after the propellant has been transferred between propellants tanks at the time indicated by the arrow 720, the calculated masses 706 increases sharply. Thereafter, the calculated masses according to the standard bookkeeping method 710', according to the bookkeeping method with losses 712', and according to the processes described above with reference to FIGS. 3, 4A, 4B, 5, and 6 trend downwardly in a similar manner as before the transfer, assuming the rate of propellant depletion does not change with time. Upon migration of propellant occurs between propellant tanks 106 and 108, the bookkeeping method becomes less accurate than prior to migration, since the known starting condition is no longer applicable. At this point, the amount of migrated propellant must be calculated using the propellant gauging method described above, and then that calculated, migrated propellant must be applied to the bookkeeping method results to establish a new starting condition for future bookkeeping method calculations.

Figure 8:
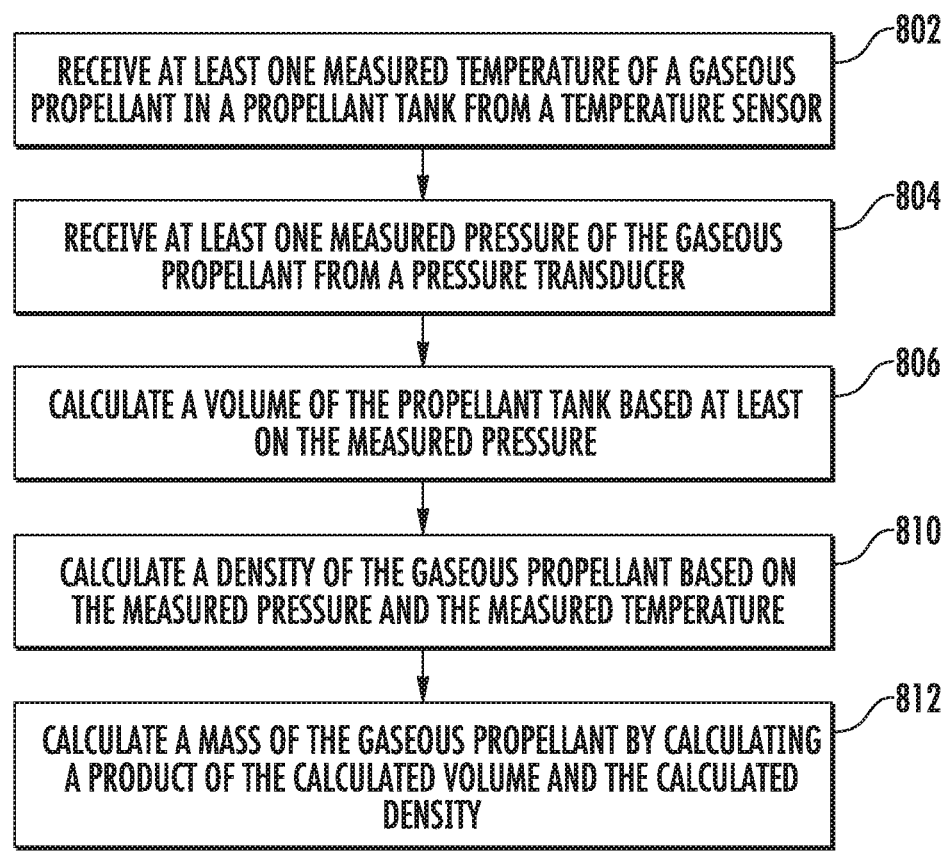
FIG. 8 is a block diagram of a process for calculating the mass of propellant in a propellant tank based on calculating the volume of a propellant tank and a density of the propellant in the propellant tank.

FIG. 8 illustrates a process 800 for calculating a mass of propellant in a propellant storage volume. In block 802, at least one measured temperature of the gaseous propellant in a propellant storage volume (e.g., a propellant tank) is received from a temperature sensor. In block 804, at least one measured pressure of the gaseous propellant is received from a pressure transducer. In block 806, a volume of the propellant storage volume based at least on the measured pressure is determined. In various aspects, the volume of the propellant storage volume may also be based on the measured temperature. In block 810, a density of the gaseous propellant based on the measured pressure and the measured temperature is determined. In block 812, a mass of the gaseous propellant is calculated by calculating a product of the determined volume and the determined density. Put differently, the determined volume is multiplied by the calculated density to determine a mass of the gaseous propellant in the propellant storage volume.

In various aspects, the decision to perform the deorbit thrust maneuver is made by personnel on the earth 150. In various aspects, the controller 220 onboard the satellite system 200 and/or the controller 230 on earth 150 could automatically perform the deorbit thrust maneuver upon the calculated mass of propellant dropping below a threshold mass. For example, the controller 220 and/or 230 could perform the deorbit thrust maneuver upon the calculated mass of propellant dropping below 5 kg. Alternatively, the controller 220 and/or 230 could stop using the remaining propellant for orbit adjustments upon the calculated mass of propellant dropping below a threshold mass to ensure sufficient propellant mass for the deorbit thrust maneuver when such a maneuver is eventually commanded by personnel on the earth 150. In various aspects, the controller 220 and/or 230 may only perform the deorbit thrust maneuver when the calculated mass, according to the process 800 discussed with reference to FIG. 8, is within an expected threshold amount of difference of the calculated mass according to another method, such as the bookkeeping method with losses 712 discussed with reference to FIG. 7, taking into consideration the inherent increase in propagated errors with time using the bookkeeping method. For example, the controller 220 and/or 230 may only perform the deorbit thrust maneuver if the two mass calculations are within 5% of one another. In the event the two mass calculations are outside of the threshold amount, the controller 220 and/or 230 could send an alert and/or alarm to personnel on earth 150 to provide a warning of the discrepancy. In one aspect, a decision to deorbit would be based on the results of the propellant gauging method described above indicating a total propellant mass that approaches the predicted mass uncertainty of the system, also taking into account trended error bars with time (per FIG. 6) and/or allocated propellant margins prior to deorbit.

The descriptions of the various aspects have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein.

Aspects described herein may take the form of an entirely hardware aspect, an entirely software aspect (including firmware, resident software, micro-code, etc.) or an aspect combining software and hardware aspects that may all generally be referred to herein as a "circuit," "module" or "system."

Aspects described herein may be a system, a method, and/or a computer program product. The computer program product may include a computer readable storage medium (or media) having computer readable program instructions thereon for causing a processor to carry out aspects disclosed herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects described herein.

Aspects are described herein with reference to flowchart illustrations and/or block diagrams of methods, apparatus (systems), and computer program products according to aspects. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to certain aspects, other and further aspects may be devised without departing from the basic scope thereof, and the scope thereof is determined by the claims that follow.

What is claimed is:

1. A satellite system, comprising:
a satellite body;
a propellant storage volume storing a gaseous propellant;
at least one thruster operable to expel the gaseous propellant;
at least one pressure transducer arranged on the propellant storage volume and operable to measure a pressure of the gaseous propellant in the propellant storage volume;
at least one temperature sensor arranged on the propellant storage volume and operable to measure a temperature of the gaseous propellant in the propellant storage volume; and
a controller that includes:
a computer processor; and
computer memory storing:
thermodynamic property data of the gaseous propellant, wherein the thermodynamic property data provides densities of the gaseous propellant at different pressures and temperatures; and
propellant storage volume data that includes known volumes of the propellant storage volume at different pressures of the gaseous propellant;
a propellant mass calculation application that, when executed on the computer processor, performs an operation for processing data, comprising:
defining a volume of the propellant storage volume, based on at least one measured pressure from the pressure transducer and the propellant storage volume data;
defining a density of the gaseous propellant in the propellant storage volume, based on the at least one measured pressure from the pressure transducer, at least one measured temperature from the temperature sensor, and the thermodynamic property data; and
calculating a mass of the gaseous propellant in the propellant storage volume, based on the defined volume and the defined density.

2. The satellite system of claim 1, wherein the controller sends thrust control commands to the at least one thruster, and wherein the controller is operable to send a deorbit thrust control command upon the calculated mass of the gaseous propellant in the propellant storage volume dropping below a threshold mass.

3. The satellite system of claim 1, wherein the tank volume data includes known volumes of the propellant storage volume at different temperatures of the gaseous propellant, and wherein the propellant mass calculation application defines the volume of the propellant storage volume based on a at least one measured temperature from the temperature sensor and the propellant storage volume data.

4. The satellite system of claim 1, wherein the at least one measured pressure includes an average of a plurality of measured pressures over the time interval, and wherein the at least one measured temperature includes an average of a plurality of measured temperatures over the time interval.

5. The satellite system of claim 1, wherein the propellant mass calculation application, when executed on the computer processor, performs additional operations for processing data, comprising:
calculating a second mass of gaseous propellant in the propellant storage volume based on a bookkeeping method; and
outputting an alert upon the calculated second mass of gaseous propellant differing from the calculated mass of the gaseous propellant based on the defined volume and the defined density by more than a threshold amount.

6. The satellite system of claim 5, wherein the controller sends thrust control commands to the at least one thruster, and wherein the controller is operable to is configured to send a deorbit thrust maneuver control command upon:
the calculated mass of the gaseous propellant in the propellant storage volume dropping below a threshold mass; and
the calculated second mass of gaseous propellant differs from the calculated mass of the gaseous propellant based on the defined volume and the defined density by less than a threshold amount.

7. The satellite system of claim 1, wherein the satellite system further comprises a second propellant storage volume storing the gaseous propellant, wherein the first and second propellant storage volumes are in fluid communication, and wherein the controller selectively operates a valve to control flow of the gaseous propellant from the second propellant storage volume to the first propellant storage volume.

8. The satellite system of claim 7, wherein the controller operates the valve to transfer gaseous propellant from the second propellant storage volume to the first propellant storage volume upon the calculated mass of gaseous propellant in the first propellant storage volume dropping below a threshold mass.

9. A method for calculating a mass of gaseous propellant in a propellant storage volume, comprising:
receiving at least one measured temperature of the gaseous propellant from a temperature sensor;
receiving at least one measured pressure of the gaseous propellant from a pressure transducer;
defining a volume of the propellant storage volume by accessing a propellant volume data structure that provides known propellant storage volumes at different tank pressures and extracting from the tank volume data structure a volume corresponding to the received at least one measured pressure of the gaseous propellant;

defining a density of the gaseous propellant in the propellant storage volume by accessing a thermodynamic property data structure that provides densities of the gaseous propellant at different pressures and temperatures and extracting from the thermodynamic property data structure a density of the gaseous propellant corresponding to the received at least one measured pressure and the at least one measured temperature; and calculating, using a computer processor, a mass of the gaseous propellant in the propellant storage volume by calculating a product of the defined volume and the defined density.

10. The method of claim 9, further comprising sending deorbit thrust control commands to at least one thruster upon the calculated mass of the gaseous propellant in the propellant storage volume dropping below a threshold mass.

11. The method of claim 9, wherein the propellant storage volume data structure includes known volumes of the propellant storage volume at different temperatures of the gaseous propellant, and wherein the volume of the propellant storage volume is calculated by extracting from the propellant storage volume data structure a volume corresponding to the received at least one measured pressure and the at least one measured temperature.

12. The method of claim 9, wherein the at least one measured pressure includes an average of a plurality of measured pressures over a time interval, and wherein the at least one measured temperature includes an average of a plurality of measured temperatures over the time interval.

13. The method of claim 9, further comprising:
  calculating a second mass of gaseous propellant in the propellant storage volume based on a bookkeeping method; and
  outputting an alert upon the calculated second mass of gaseous propellant differs from the calculated mass of the gaseous propellant based on the defined volume and the defined density by more than a threshold amount.

14. The method of claim 13, further comprising sending deorbit thrust control commands to at least one thruster upon:
  the calculated mass of the gaseous propellant in the propellant storage volume dropping below a threshold mass; and
  the calculated second mass of gaseous propellant differs from the calculated mass of the gaseous propellant based on the defined volume and the defined density by less than a threshold amount.

15. A computer program product for calculating a mass of gaseous propellant in a propellant storage volume, the computer program product comprising:
  a computer-readable storage medium having computer-readable program code embodied therewith, the computer-readable program code executable by one or more computer processors to:
  receive at least one measured temperature of the gaseous propellant from a temperature sensor;
  receive at least one measured pressure of the gaseous propellant from a pressure transducer;
  define a volume of the propellant storage volume by accessing a propellant storage volume data structure that provides known propellant storage volumes at different propellant storage volume pressures and extracting from the propellant storage volume data structure a volume corresponding to the received at least one measured pressure of the gaseous propellant;
  define a density of the gaseous propellant in the propellant storage volume by accessing a thermodynamic property data structure that provides densities of the gaseous propellant at different pressures and temperatures and extracting from the thermodynamic property data structure a density of the gaseous propellant corresponding to the received at least one measured pressure and the at least one measured temperature; and
  calculate a mass of the gaseous propellant in the propellant storage volume by calculating a product of the defined volume and the defined density.

16. The computer program product of claim 15, wherein the computer-readable program code is further executable to send deorbit thrust control commands to at least one thruster upon the calculated mass of the gaseous propellant in the propellant storage volume dropping below a threshold mass.

17. The computer program product of claim 15, wherein the propellant storage volume data structure includes known volumes of the propellant storage volume at different temperatures of the gaseous propellant, and wherein the volume of the propellant storage volume is calculated by extracting from the propellant storage volume data structure a volume corresponding to the received at least one measured pressure and the at least one measured temperature.

18. The computer program product of claim 15, wherein the at least one measured pressure includes an average of a plurality of measured pressures over a time interval, and wherein the at least one measured temperature includes an average of a plurality of measured temperatures over the time interval.

19. The computer program product of claim 15, herein the computer-readable program code is further executable to:
  calculate a second mass of gaseous propellant in the propellant storage volume based on a bookkeeping method; and
  output an alert upon the calculated second mass of gaseous propellant differs from the calculated mass of the gaseous propellant based on the defined volume and the defined density by more than a threshold amount.

20. The computer program product of claim 19, wherein the computer-readable program code is further executable to send deorbit thrust control commands to at least one thruster upon:
  the calculated mass of the gaseous propellant in the propellant storage volume dropping below a threshold mass; and
  the calculated second mass of gaseous propellant differs from the calculated mass of the gaseous propellant based on the defined volume and the defined density by less than a threshold amount.

* * * * *